United States Patent [19]

Collins

[11] Patent Number: 4,593,679

[45] Date of Patent: Jun. 10, 1986

[54] CONNECTOR DEVICE FOR AN ENDOSCOPE

[75] Inventor: Ian P. Collins, Welwyn, England

[73] Assignee: Warner-Lambert Technologies, Inc., Southbridge, Mass.

[21] Appl. No.: 697,807

[22] Filed: Feb. 4, 1985

[30] Foreign Application Priority Data

Feb. 9, 1984 [GB] United Kingdom ............... 8403431

[51] Int. Cl.[4] .............................................. A61B 1/00
[52] U.S. Cl. ......................................... 128/4; 74/352; 74/462
[58] Field of Search ................ 128/4, 6; 74/352, 353, 74/354, 460, 462, DIG. 10; 434/401

[56] References Cited

U.S. PATENT DOCUMENTS 1,481,720  1/1924  Ljungstrom ......................... 74/354

Primary Examiner—William H. Grieb
Attorney, Agent, or Firm—Alan H. Spencer

[57] ABSTRACT

An endoscope has a handle portion and a separate shaft portion which can be joined to the handle portion. The shaft portion has a flexible shaft flexing movement of which is controlled by knobs on the handle portion, and this motion is transmitted across the handle/shaft interface by meshing gearwheels. Each tooth of each gearwheel has a crown shaped so as to have a central ridge between sloping sides which facilitate interengagement of the gearwheels when the latter are brought into crown-to-crown engagement in a non-rotating condition.

3 Claims, 3 Drawing Figures

CONNECTOR DEVICE FOR AN ENDOSCOPE

DESCRIPTION

1. Field of the Invention

This invention relates to endoscopes, which are medical instruments for inspecting the cavities of internal organs.

2. Background to the Invention

Our U.K Patent Application No. 8319980 discloses an endoscope with a separable handle and shaft. Control knobs on the handle move the distal end of the shaft, and movement is transmitted across the handle/shaft interface by meshing gearwheels. Since neither gearwheel is rotating when the gearwheels are brought together it is possible for the teeth to abut crown-to-crown and in consequence to fail to mesh. The invention aims to provide an endoscope avoiding this problem.

SUMMARY OF THE INVENTION

According to the invention an endoscope has a shaft and a separable handle and a mechanism for transmitting motion from the handle to the shaft, the mechanism comprising two rotatable gearwheels which are respectively rotatably mounted in the handle and shaft and which are capable of being taken into and out of engagement by relative movement of the handle and shaft, wherein each gearwheel has teeth each of which has a crown shaped so as to have a central ridge positioned between sloping sides which extend from the ridge to the corresponding face of the tooth, the sloping sides of the crowns facilitating interengagement of the gearwheels when the latter are brought into crown-to-crown engagement in a non-rotating condition.

Hence, in the invention the sides of each tooth crown are shaped so that when they come into contact the interaction of one side upon the other effects sufficient rotation of one or other (or both) gearwheels that the teeth mesh smoothly with one another, without there being any risk of the crowns abutting and preventing interengagement of the gearwheels.

Preferably the sides are planar, the minimum angle of inclination (to a notional planar crown) being a function of the coefficient of friction of the material (or materials) of the gearwheels. To a first approximation, the tangent of the angle of inclination of each side is equal to the coefficient of friction of the two gearwheels. For plastic materials, the angle is preferably between 20° and 30°, and for acetal 25° has been found to be suitable.

The mechanism preferably transmits from the handle to the shaft motion which causes flexing of the remote or distal end of the shaft under the control of movement applied to adjusting members such as control knobs on the endoscope handle. Preferably the handle has a pair of gearwheels and the shaft has a pair of gearwheels respectively engaged with the pair of gearwheels of the handle, the two pairs of gearwheels providing for controlled flexing of the shaft in two mutually orthogonal planes.

The invention will now be further described by way of example with reference to the accompanying drawings in which.

Figure 1:
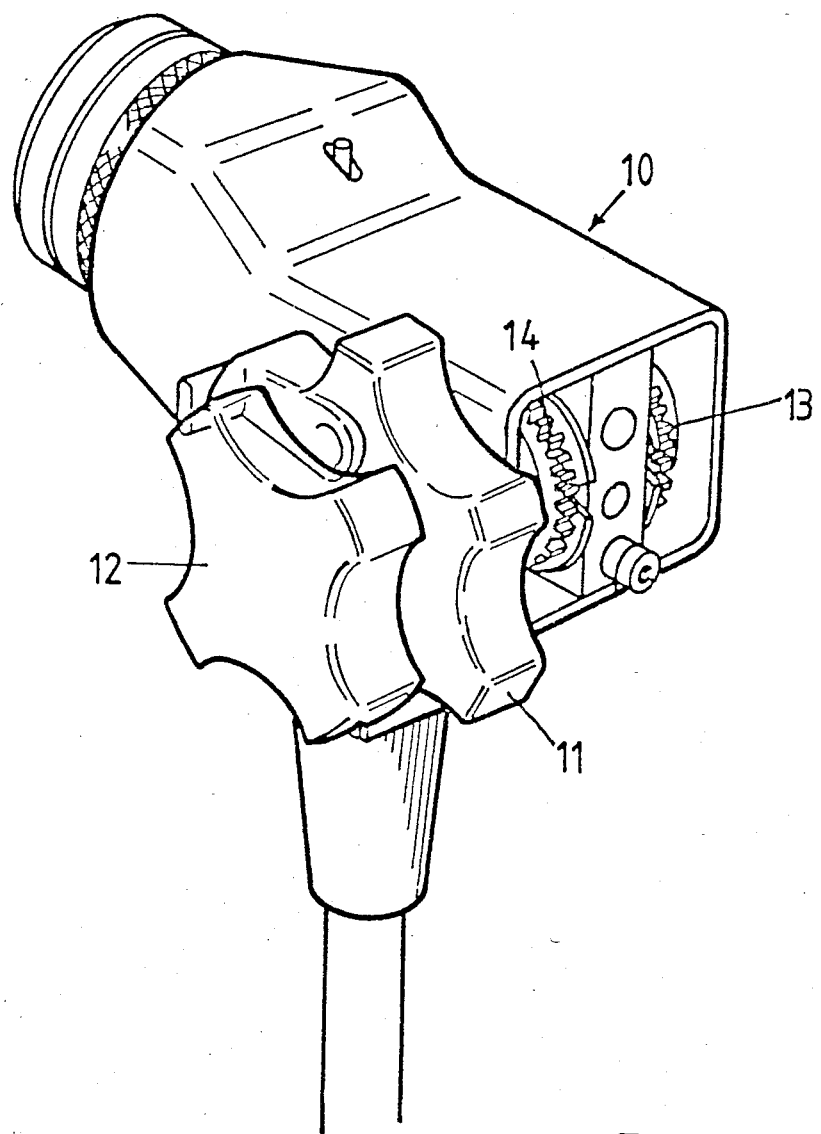
FIG. 1 shows a handle portion of an endoscope.
Figure 2:
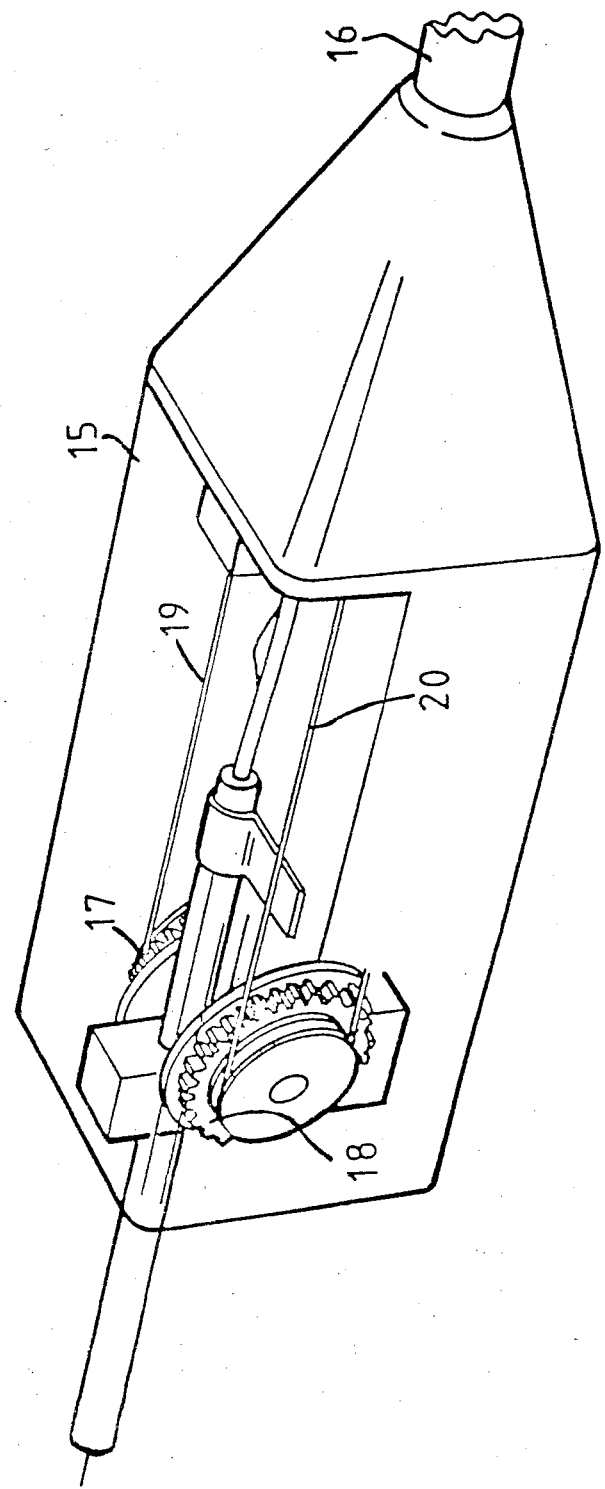
FIG. 2 shows a portion of the shaft end of the endoscope which mates with the handle portion.

FIG. 1 shows a handle portion 10 which has two rotatable knobs 11,12 for transmitting movement to respective gearwheels 13,14. When the handle portion 10 and the shaft portion 15 are brought together, the gearwheels 13,14 respectively mesh with gearwheels 17,18 on the shaft portion 15. The shaft portion 15 has a flexible shaft 16, and flexing movement of the distal end of the shaft 16 is effected by controlled rotation of the knobs 11,12, as disclosed in U.K. Patent Application 8319980. The handle portion 10 and the shaft portion 15 are separable and the movement imparted to the knobs 11, 12 is transmitted across the handle/shaft interface by means of the meshing gearwheels. The meshing gearwheels transmit movement to respective tension elements 19,20 which provide for flexing of the distal end of the shaft 16 in the two mutually orthogonal planes.

Since the gearwheels 13,14; 17,18 are brought into mesh with the gearwheels in a non-rotating condition, it is possible for teeth on the two gearwheels to abut in crown-to-crown relationship. If this happens, the teeth are not brought into mesh.

Figure 3:
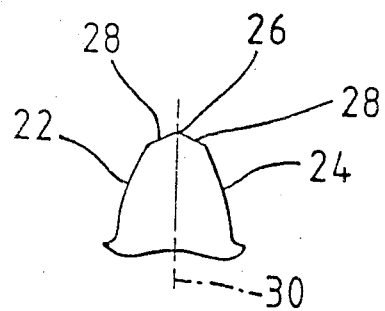
FIG. 3 shows the shape of a tooth of a gearwheel of a mechanism for transmitting motion across the handle/shaft interface.

By recourse to the invention the gearwheels are provided with teeth having the profile shown in FIG. 3. Each tooth has opposed, curved faces 22, 24 which converge towards the tooth crown. The crown has a central ridge 26 positioned between sloping sides 28 which extend from the ridge 26 to the corresponding face 22 or 24. Each side 28 of the crown is planar and is inclined at an angle of about 65° to the central axis 30 of the tooth.

I claim:

1. An endoscope having a shaft, a handle separable from the shaft and a mechanism for transmitting motion from the handle to the shaft, the mechanism comprising two rotatable gearwheels which are respectively rotatably mounted in the handle and shaft and which are capable of being taken into and out of engagement by relative movement of the handle and shaft, wherein each gearwheel has teeth each of which has a crown shaped so as to have a central ridge positioned between sloping sides which extend from the ridge to the corresponding face of the tooth, the sloping sides of the crowns facilitating interengagement of the gearwheels when the latter are brought into crown-to-crown engagement in a non-rotating condition, said crown sides being planar, the minimum angle of inclination (to a notional planar crown) being a function of the coefficient of friction of the material of the gearwheels, said minimum angle ranging between 20° and 30°.

2. An endoscope according to claim 1, wherein the gearwheels are fabricated of acetal and said minimum angle is 25°.

3. An endoscope according to claim 1, wherein the handle has a pair of gearwheels and the shaft has a pair of gearwheels respectively engaged with the pair of gearwheels of the handle, the two pairs of gearwheels providing for controlled flexing of the shaft in two mutually orthogonal planes.

* * * * *